United States Patent [19]

McRae

[11] Patent Number: Plant 6,202

[45] Date of Patent: Jun. 14, 1988

[54] HYBRID ASIATIC LILY NAMED SUNFLIGHT

[75] Inventor: Edward A. McRae, Boring, Oreg.

[73] Assignee: Melridge Inc., Gresham, Oreg.

[21] Appl. No.: 861,916

[22] Filed: May 12, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid lily plant bearing large clusters of flowers of large size, excellent form and long persistence, the flowers being particularly characterized by their unusual color pattern which combines the soft cream yellow base color with a rich gold flush at the center of the tepal body, the tepals carrying an unusual spotting pattern characterized by a narrow group of tiny spots adjacent the end of the nectary and on each side of the midrib channel. The flowers of this new variety have long persistence, both on the plant and as cut flowers; the plant is highly resistant to disease and shows high tolerance to virus, making it an excellent garden plant. It is vigorous in growth and is a good propagator and the bulbs may be precooled and forced for cut flower production, the plant being well suited to mass commercial cultivation.

1 Drawing Sheet

BACKGROUND OF THE INVENTION

This new variety of lily plant originated as a seedling selected from a group of seedlings planted at Sandy, Oreg., in the course of my breeding efforts with the object of producing new varieties of lilies in pastel yellow color tone which would be well suited for forcing for cut flower production out-of-season. These seedlings were the result of my crossing the clonal cultivar 'Connecticut King' as the seed parent and the clonal cultivar 'Sunrise' as the pollen parent, both being unpatented varieties.

This particular seedling was selected by me for propagation because of the large size and upright orientation of its flowers, which have a soft cream-yellow/rich gold color pattern accentuated by an unusual dainty grouping of spots on each side of the midrib channel adjacent the end of the nectary on each tepal, the large flowers being carried on a single stalk and appearing to possess the excellence of form, color and habit that would well satisfy my breeding objectives.

This selected plant was asexually reproduced by me and under my direction at Sandy, Oreg., by bulb scale propagation with such satisfactory results that propagation was carried on at Sandy, Oreg., through several successive generations by bulb scale propagation as well as by natural propagation from bulblets.

The successive generations of this new plant have demonstrated that this clone possesses to a high degree the desirable characteristics of hybrid vigor, great hardiness and disease resistance, and that these characteristics hold true from generation to generation under asexual propagation and appear to be firmly fixed.

DESCRIPTION OF THE DRAWING

My new variety of lily plant is illustrated by the accompanying photographic drawing, which shows a full face view of the open bloom in full color and illustrates the flower form and tepal arrangement and, in particular, the novel and distinctive, lightly spotted, cream-yellow and gold flower colors.

DESCRIPTION OF THE NEW VARIETY

The following is a detailed description of my new variety of Asiatic hybrid lily with nomenclature according to The International Lily Register of The Royal Horticultural Society of London (Second Edition, 1969), and with color designations according to The R.H.S. Colour Chart published in 1966.

THE PLANT

Origin: Seedling.

Parentage:

*Seed parent.*—Lilium 'Connecticut King' (unpatented).

*Pollen parent.*—Lilium 'Sunrise' (unpatented).

Classification:

*Horticultural.*—Division I-A, Upright Asiatic Hybrid Lily (Horticultural Classification of Lilies, The Royal Horticultural Society of London).

*Commercial.*—Upright Asiatic Hybrid Lily.

Form: Single stem, erect and stately.

Height: About 100 to 110 cm. from bulbs of about 15 to 18 cm. in circumference.

Growth: Upright and vigorous.

Foliage:

*Quantity.*—Abundant.

*Leaf size.*—About 8 to 10 cm. long and 0.7 to 1.0 cm. wide.

*Leaf shape.*—Lanceolate with acuminate tip.

*Texture.*—Leathery.

*Aspect.*—Glossy.

*Color.*—Dark green, lighter on the under side.

Bulbs:

*Size.*—Various, ranging up to about 25 cm. in circumference for commercial use.

*Color.*—White.

THE BUD

Form: Long ovoid with obtuse apex.

Size: About 8 to 9 cm. long and about 5 cm. in circumference just prior to opening.

Opening rate: The bud opens slowly, taking about an hour in response to morning light.

Color: Soft cream underlying soft green just prior to opening and as the tepals begin to unfurl; the base of the bud may be lightly flushed with pink.

Peduncle:

*Length.*—About 4 to 6 cm. in average, but it may elongate somewhat if light levels are too low.

*Color.*—Dark green with plum overlay.

THE FLOWER

Blooming habit: Annually, once and profusely in mid-season.

Size: Large; about 16 to 18 cm. in diameter.

Borne: As a raceme on a single stem having 9 to 11 buds (from a bulb about 18 cm. in circumference).

Shape: Cup-shaped upon first opening and becoming flattened as the tepals recurve by the second day.

Tepalage:

*Number.*—Six, hexagonally arranged and imbricated.

*Size.*—Outer tepals — About 2 to 2.5 cm. wide. Inner tepals — About 3 cm. wide.

*Color.*—The flowers are distinguished by their unusual color pattern, the base color being a soft cream-yellow, 4C, shading to 4D at the tepal margins and tip. A flush of rich golden yellow, 12A-B, covers the base portion of the tepal in an area about 2 cm. wide and 2 cm. long extending above the nectaries. The nectaries are green.

*Spotting.*—There is a small group of tiny deep magenta spots on each side of the midrib channel and just above the nectaries. Collectively, on both the inner and outer tepals, the spots form a ring about 4 to 5 cm. in diameter and about 1 cm. wide as the flower is seen from a full face view.

*Longevity.*—The tepals stay on the stems about three weeks.

*Appearance.*—The flower is shiny.

*Color changes.*—There is little color change as the flower ages, if the light levels are adequate for cut flower maintenance. The gold flush may soften slightly to 12C.

Peduncle:

*Length.*—About 6 to 10 cm., in average.

*Form.*—Sturdy and ascending up to 45° from the horizontal. Very rarely is there an occurrence of secondary buds.

*Color.*—Dark green with plum overlay.

Disease resistance: The flower and plant are resistant to diseases and, in particular, they are resistant to Fusarium Bulb Rot and Botrytis Blight.

Fragrance: None.

Lasting quality: The flower is long lasting, both on the plant and as a cut flower.

REPRODUCTIVE ORGANS

Stamens:

*Number.*—Six.

*Arrangement.*—Typical of genus Lilium.

Anthers and pollen: Greyed orange, 171A.

Filaments:

*Length.*—About 5 cm.

*Color.*—Soft yellow, 4D.

Pistils:

*Number.*—One.

*Length.*—About 5 cm.

Stigma:

*Color.*—Soft green with deep plum overlay.

Characteristics of ovary: The ovary is characteristic of genus Lilium.

THE FRUIT

Fertility: The fruit is fertile.

Shape: Ovoid.

Color at maturity: Soft brown, sometimes overlaid with soft plum.

This new lily variety most closely resembles 'Connecticut King' but it has a softer cream-yellow base color and a dainty arrangement of spots which collectively form a ring around the blossom center as seen from a face view of a flower. This new variety also has much broader tepals and a better flower form than 'Connecticut King', as well as a more regular and symmetrical inflorescence free of the regular secondary buds of 'Connecticut King'.

I claim:

1. A new and distinctive variety of Asiatic hybrid lily, substantially as herein shown and described, characterized by its large, broad tepalled flowers of soft cream base color enriched by a gold blush at the tepal base and further distinguished by a group of tiny spots adjacent the end of each nectary which collectively form a ring around the center of the flower just beyond the ends of the nectary channels; this plant being further characterized by its vigorous growth and rapid natural propagation, the excellence of its flower form, and its versatility both as a garden plant and as a cut flower producer from precooled bulbs forced under glass out-of-season.

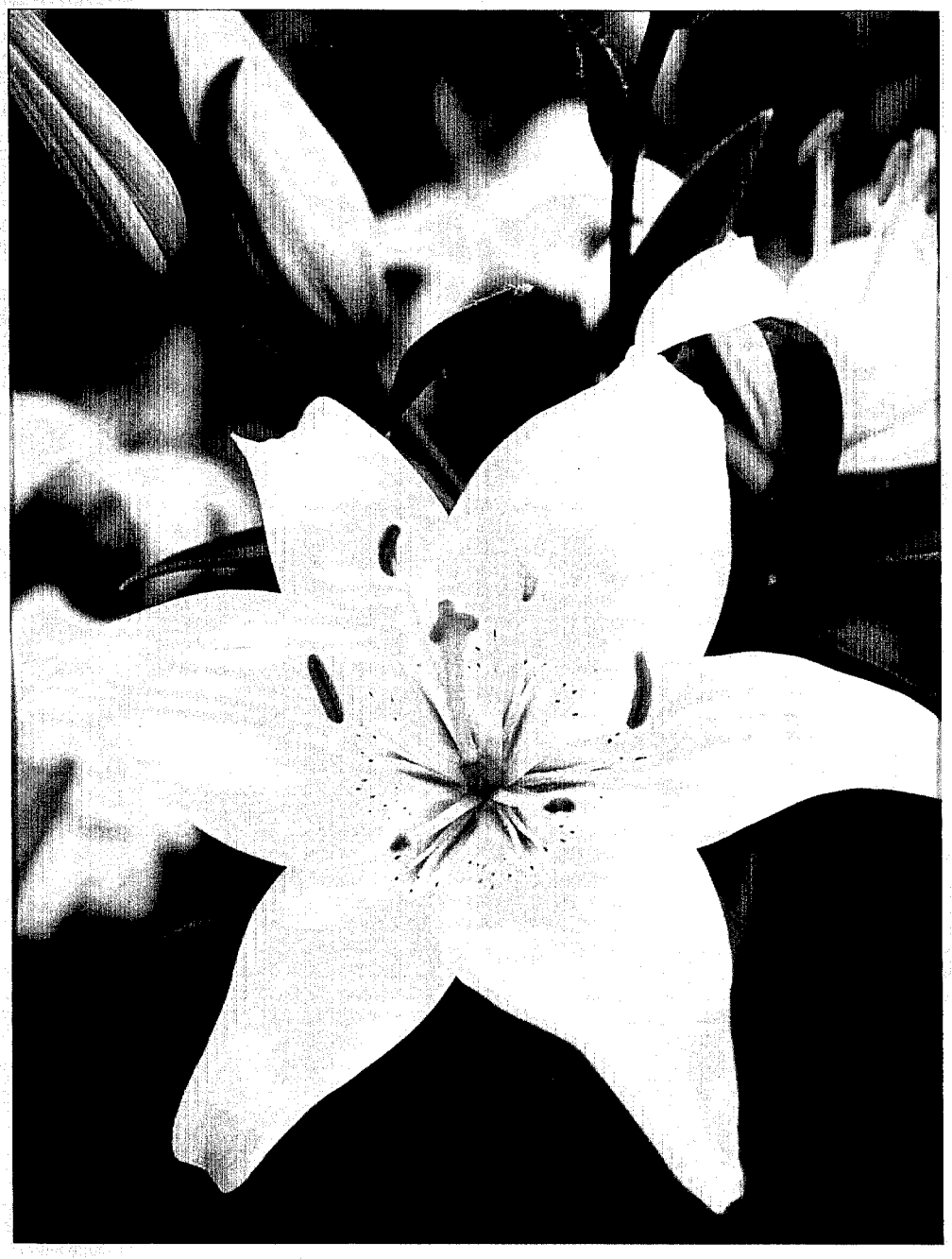

* * * * *